(12) United States Patent
Yamanaka

(10) Patent No.: US 11,083,480 B2
(45) Date of Patent: *Aug. 10, 2021

(54) GRIPPING MECHANISM AND GRIPPING TOOL

(71) Applicant: OLYMPUS CORPORATION, Tokyo (JP)

(72) Inventor: Noriaki Yamanaka, Tokyo (JP)

(73) Assignee: OLYMPUS CORPORATION, Tokyo (JP)

( * ) Notice: Subject to any disclaimer, the term of this patent is extended or adjusted under 35 U.S.C. 154(b) by 374 days.

This patent is subject to a terminal disclaimer.

(21) Appl. No.: 16/199,330

(22) Filed: Nov. 26, 2018

(65) Prior Publication Data

US 2019/0090894 A1 Mar. 28, 2019

Related U.S. Application Data

(63) Continuation of application No. PCT/JP2016/067111, filed on Jun. 8, 2016.

(51) Int. Cl.
*A61B 17/28* (2006.01)
*B25J 15/02* (2006.01)
(Continued)

(52) U.S. Cl.
CPC .......... *A61B 17/2816* (2013.01); *A61B 17/28* (2013.01); *B25J 15/0233* (2013.01);
(Continued)

(58) Field of Classification Search
CPC ........ A61B 17/2816; A61B 2017/2947; A61B 2017/2939; A61B 17/29; A61B 34/71; B25J 15/0233; B25J 15/08; B25J 15/083
See application file for complete search history.

(56) References Cited

U.S. PATENT DOCUMENTS

| 5,507,773 A | 4/1996 | Huitema et al. |
| 5,562,700 A | 10/1996 | Huitema et al. |

(Continued)

FOREIGN PATENT DOCUMENTS

| EP | 0668057 A2 | 8/1995 |
| EP | 0800792 A1 | 10/1997 |

(Continued)

OTHER PUBLICATIONS

International Search Report dated Sep. 6, 2016 issued in PCT/JP2016/067111.

(Continued)

*Primary Examiner* — Katherine H Schwiker
(74) *Attorney, Agent, or Firm* — Scully, Scott, Murphy & Presser, P.C.

(57) ABSTRACT

A gripping mechanism includes: two gripping pieces pivoted relative to each other about a pivot axis; a base supporting at least one of the gripping pieces; a pulley rotatably supported about a rotation axis parallel to the pivot axis; a wire wound around the pulley, causing tensile forces that move the rotation axis in one direction to act, and transmitting a pressing force; and a force-receiving portion receiving the pressing force. The pulley is disposed so that a resultant force of the tensile forces of the wire acting on the rotation axis generates a moment causing the gripping pieces to be pivoted in a direction causing the gripping pieces to be closed. The force-receiving portion is disposed so that the pressing force applied from the wire generates a moment causing the gripping pieces to be pivoted in a direction causing the gripping pieces to be opened.

10 Claims, 7 Drawing Sheets

(51) Int. Cl.
*B25J 15/08* (2006.01)
*A61B 17/29* (2006.01)
*A61B 34/00* (2016.01)

(52) U.S. Cl.
CPC ............. *B25J 15/083* (2013.01); *A61B 17/29* (2013.01); *A61B 34/71* (2016.02); *A61B 2017/2939* (2013.01); *A61B 2017/2947* (2013.01)

(56) References Cited

U.S. PATENT DOCUMENTS

| | | | |
|---|---|---|---|
| 5,562,701 A | 10/1996 | Huitema et al. | |
| 5,562,702 A | 10/1996 | Huitema et al. | |
| 5,582,617 A * | 12/1996 | Klieman | A61B 17/29 606/170 |
| 6,206,903 B1 | 3/2001 | Ramans | |
| 6,896,704 B1 * | 5/2005 | Higuchi | B25J 15/0009 623/64 |
| 7,316,681 B2 | 1/2008 | Madhani et al. | |
| 8,333,780 B1 * | 12/2012 | Pedros | A61B 34/30 606/174 |
| 2002/0040217 A1 | 4/2002 | Jinno | |
| 2004/0093019 A1 * | 5/2004 | Kothe | A61B 17/29 606/205 |
| 2004/0267406 A1 | 12/2004 | Jinno | |
| 2006/0167589 A1 | 7/2006 | Jinno | |
| 2007/0288044 A1 | 12/2007 | Jinno et al. | |
| 2008/0232932 A1 | 9/2008 | Jinno | |
| 2012/0239011 A1 | 9/2012 | Hyodo et al. | |
| 2015/0025571 A1 * | 1/2015 | Suzuki | A61B 17/29 606/205 |
| 2015/0173787 A1 * | 6/2015 | Frings | A61B 17/3201 606/174 |
| 2018/0050456 A1 | 2/2018 | Yamanaka | |

FOREIGN PATENT DOCUMENTS

| | | | |
|---|---|---|---|
| EP | 1 195 151 A1 | 4/2002 | |
| EP | 1854418 A1 | 11/2007 | |
| EP | 2 666 429 A1 | 11/2013 | |
| JP | 01-199777 * | 8/1989 | ................ B25J 1/00 |
| JP | H08-033628 A | 2/1996 | |
| JP | 2000-325375 A | 11/2000 | |
| JP | 2001-314410 A | 11/2001 | |
| JP | 2002-102248 A | 4/2002 | |
| JP | 2007-301692 A | 11/2007 | |
| JP | 2011-083476 A | 4/2011 | |
| JP | 2012-187311 A | 10/2012 | |
| WO | WO 2016/194067 A1 | 12/2016 | |
| WO | WO 2016/194777 A1 | 12/2016 | |

OTHER PUBLICATIONS

International Search Report and Written Opinion of the International Searching Authority dated Aug. 9, 2016 received in PCT/JP2016/065962.

* cited by examiner

GRIPPING MECHANISM AND GRIPPING TOOL

CROSS-REFERENCE TO RELATED APPLICATIONS

This is a continuation of International Application PCT/JP2016/067111 which is hereby incorporated by reference herein in its entirety.

TECHNICAL FIELD

The present invention relates to a gripping mechanism and a gripping tool.

BACKGROUND ART

An example of a known gripping mechanism that grips a subject, such as a living tissue, by using a pair of pivotably connected gripping pieces is a gripping mechanism equipped with two wires for opening and closing the pair of gripping pieces, namely, a wire used for opening and a wire used for closing (for example, refer to PTL 1 and PTL 2).

CITATION LIST

Patent Literature

{PTL 1} Japanese Unexamined Patent Application, Publication No. 2011-83476
{PTL 2} U.S. Pat. No. 7,316,681

SUMMARY OF INVENTION

One aspect of the present invention provides a gripping mechanism including: two gripping pieces that are pivoted relative to each other about a pivot axis; a base that supports at least one of the gripping pieces at a distal-end portion in a pivotable manner; a pulley that is supported so as to be rotatable about a rotation axis that is parallel to the pivot axis; a wire that is wound around the pulley, in which one end thereof is secured to one of the gripping pieces or the base, and that causes, with a pulling force applied to the other end thereof, tensile forces that move the rotation axis in one direction to act on both sides of the pulley, between which the rotation axis is interposed, the wire transmitting a pressing force applied to the other end; and a force-receiving portion that receives the pressing force transmitted through the wire, wherein the pulley is disposed so that a resultant force of the tensile forces of the wire acting on the rotation axis generates a moment that causes the gripping pieces to be pivoted in a direction that causes the gripping pieces to be closed relative to each other, and the force-receiving portion is disposed so that the pressing force applied from the wire generates a moment that causes the gripping pieces to be pivoted in a direction that causes the gripping pieces to be opened relative to each other.

DESCRIPTION OF EMBODIMENTS

A gripping mechanism 3 and a gripping tool 1 provided with the gripping mechanism 3 according to the first embodiment of the present invention will now be described with reference to the drawings.

Figure 1:
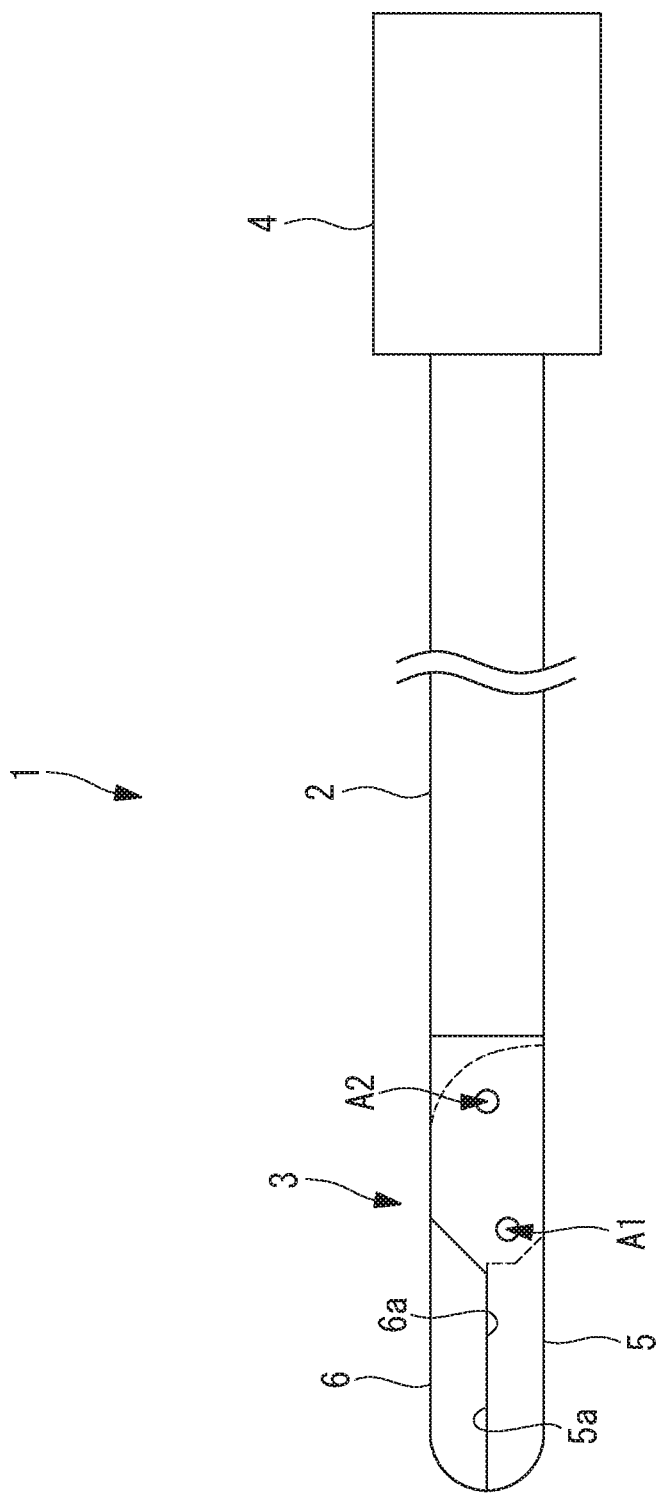
FIG. 1 is an overall diagram showing a gripping tool according to one embodiment of the present invention.

The gripping tool 1 according to this embodiment is a medical equipment that is used when gripping a subject such as living tissue. As shown in FIG. 1, the gripping tool 1 includes an elongated body portion (base) 2 that can be inserted into a body, the gripping mechanism 3 that is provided at a distal end of the body portion 2, and a driving portion 4 that is connected to a proximal end of the body portion 2.

Figure 2:
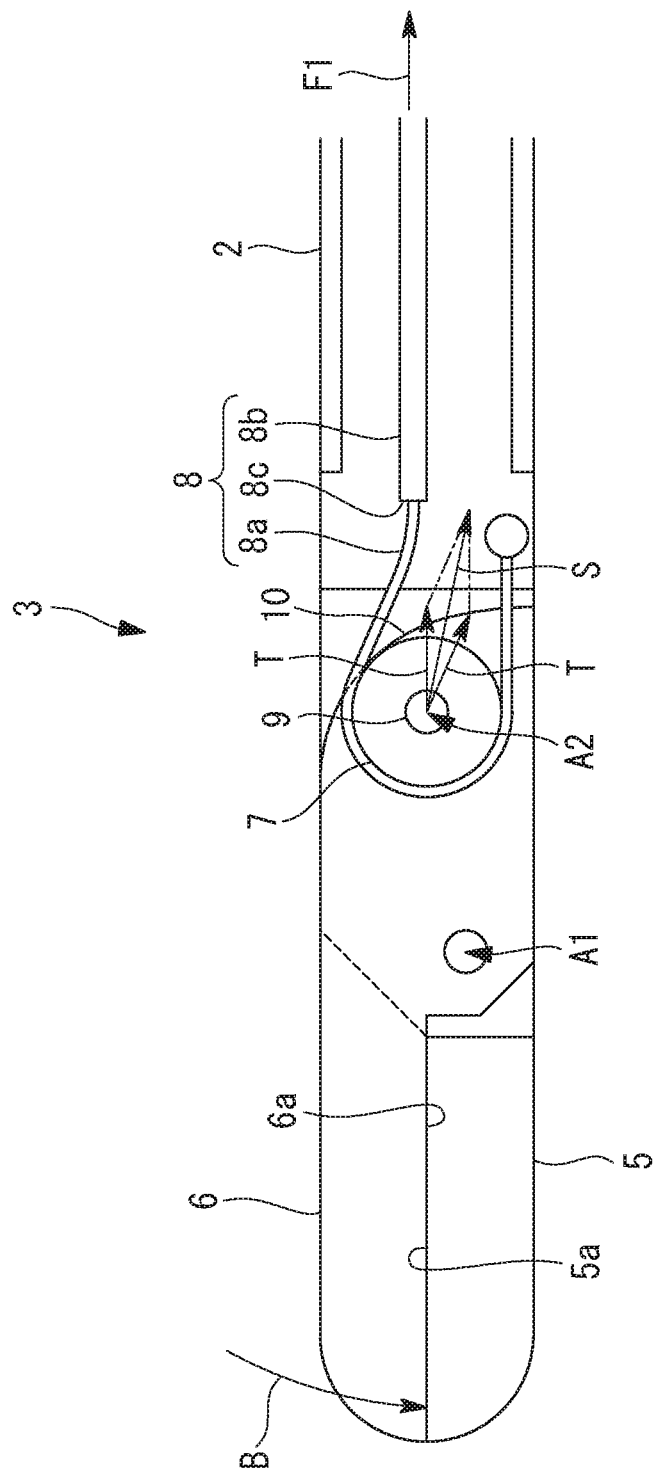
FIG. 2 is a vertical sectional view showing a gripping mechanism according to a first embodiment of the present invention, in which two gripping pieces are in a closed state.
Figure 3:
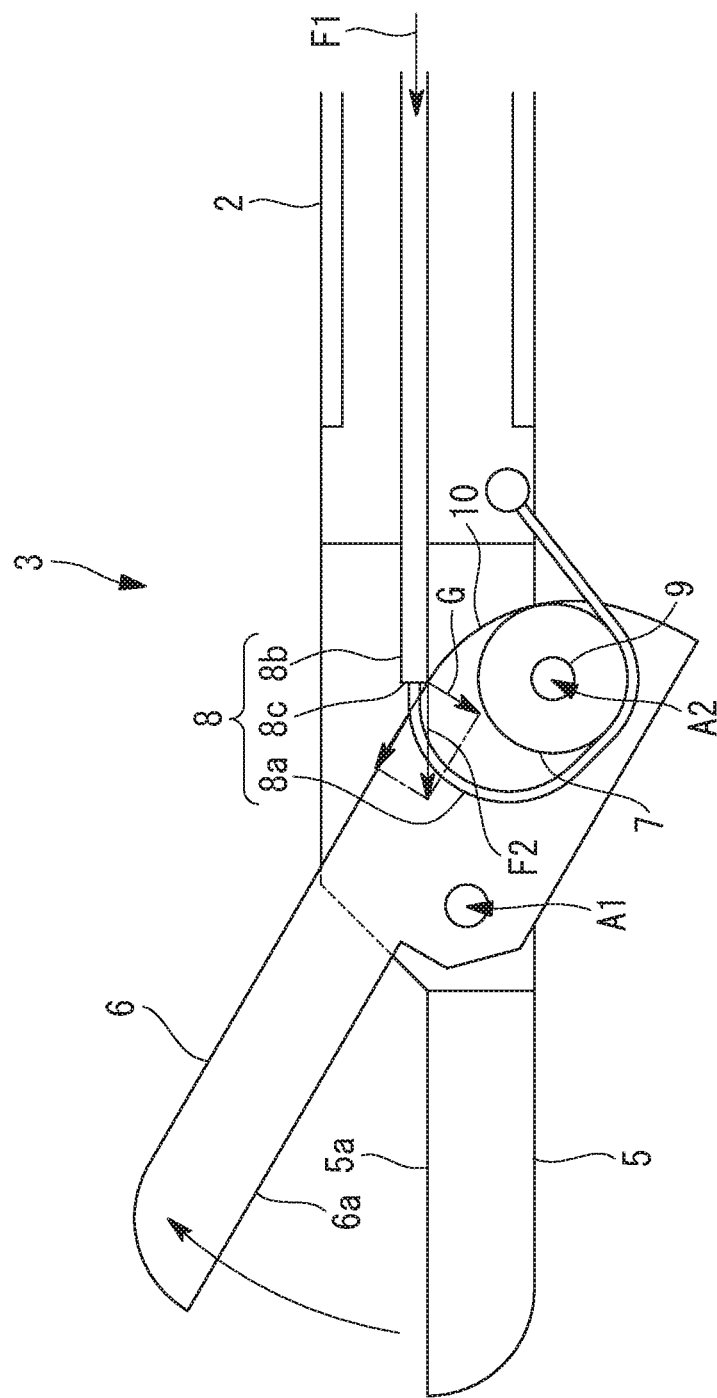
FIG. 3 is a vertical sectional view showing a state in which the two gripping pieces of the gripping mechanism shown in FIG. 2 are open.

As shown in FIG. 2 and FIG. 3, the gripping mechanism 3 of this embodiment includes a first gripping piece (gripping piece) 5, a second gripping piece (gripping piece) 6, a pulley 7, and a wire 8. The first gripping piece is secured to a distal end portion of the body portion 2. The second gripping piece 6 is joined with the first gripping piece 5 so as to be pivotable about a pivot axis A1 that is orthogonal to the longitudinal axis of the body portion 2. The pulley 7 is supported by the second gripping piece 6 so as to be rotatable about a rotation axis A2 that is parallel to the pivot axis A1. The wire 8 is wound around the pulley 7. FIG. 2 shows a closed state in which the second gripping piece 6 is closed with respect to the first gripping piece 5.

The first gripping piece 5 has a first gripping surface 5a on a distal-end side thereof, and the second gripping piece 6 has a second gripping surface 6a on a distal-end side thereof. The first gripping piece 5 and the second gripping piece 6 are individually disposed in directions along the longitudinal direction of the body portion 2 so that the gripping surfaces 5a and 6a face each other.

The pivot axis A1 that connects the second gripping piece 6 to the first gripping piece 5 in a pivotable manner is disposed farther on the proximal-end side than the first gripping surface 5a and the second gripping surface 6a are. As a result of the second gripping piece 6 pivoting about the pivot axis A1, the distal ends of the first gripping piece 5 and second gripping piece 6 are opened and closed.

The pulley 7 is supported, in a rotatable manner, by a shaft 9, which is co-axial with the rotation axis A2 of the pulley 7, farther on the proximal-end side than the pivot axis A1 of the second gripping piece 6 is.

The wire 8 is disposed inside the body portion 2 in the longitudinal direction thereof. After the wire 8 is wound approximately half way around the pulley 7 on a distal-end side on an outer circumferential surface, the distal end of the wire 8 is secured to the body portion 2 farther on the proximal-end side than the rotation axis A2 is. The proximal end portion of the wire 8 is connected to the driving portion 4.

In this embodiment, the wire 8 has a distal-end-side portion 8a wound around the pulley 7, and a proximal-end-side portion 8b on the proximal-end side with respect to the distal-end-side portion 8a. The distal-end-side portion 8a of the wire 8 has an outer diameter sufficiently smaller than that of the proximal-end-side portion 8b, and is highly flexible. In contrast, the proximal-end-side portion 8b has an outer diameter sufficiently larger than that of the distal-end-side portion 8a, and has high flexural rigidity. A level-difference portion (pressing portion) 8c is disposed at the border between the distal-end-side portion 8a and the proximal-end-side portion 8b.

The distal-end-side portion 8a of the wire 8 is wound substantially half way around the pulley 7, and two portions of the wire 8 that respectively extend in two tangential directions of the pulley 7 are disposed so as to be substantially parallel to each other.

The driving portion 4 has a motor (not shown) connected to the proximal end of the wire 8. A tensile force is generated in the wire 8 by pulling the wire 8 toward the proximal end by operating the motor, and the wire 8 is pressed toward the distal-end side so as to generate a pressing force to be transmitted through the wire 8.

Moreover, in this embodiment, an inclined surface (force-receiving portion) 10 is disposed on the proximal-end side of the second gripping piece 6. The inclined surface 10 is inclined such that a line perpendicular thereto passes through the rotation-axis-A2-side with respect to the pivot axis A1. In this embodiment, the inclined surface 10 is formed of a curved surface having a gradually changing inclination angle. The inclined surface 10 is positioned so as to allow the distal-end-side portion 8a of the wire 8 to pass through but causes the level-difference portion 8c at the border with the proximal-end-side portion 8b to abut thereagainst. The inclined surface 10 is not limited to a curved surface and may be formed as a straight, flat surface.

The operation of the gripping mechanism 3 and the gripping tool 1 according to this embodiment having the above-described configuration will now be described.

With the gripping tool 1 according to this embodiment, as a result of the wire 8 being pulled toward the proximal end by operating the driving portion 4, tensile force T that are substantially equal to a pulling force F1 are generated in the individual portions of the wire 8.

As shown in FIG. 2, when the wire 8 is brought into close contact with the outer circumferential surface of the pulley 7 on the distal-end side, substantially equal tensile forces T are also individually generated in two portions of the wire 8 that are disposed so as to be substantially parallel to each other with the rotation axis A2 of the pulley 7 existing therebetween. As a result, as indicated by arrows in FIG. 2, a resultant force S whose magnitude is two times greater than that of the tensile force T acts on the rotation axis A2 of the pulley 7. Therefore, the pulling force F1 is amplified twofold as a result.

In other words, according to the gripping mechanism 3 of this embodiment, the wire 8 is wound substantially half way around the pulley 7. Thus, it is possible to generate a moment that allows the second gripping piece 6 to be pivoted at a force amplified substantially twofold relative to the pulling force F1 applied to the proximal end of the wire 8. In other words, there is an advantage in that the tissue can be firmly gripped with a large force although the pulling force F1 applied to the proximal end of the wire 8 is small.

Next, in order to open the two gripping pieces 5 and 6 of the gripping tool 1 of this embodiment, the driving portion 4 is actuated to apply, to the wire 8, a pressing force F2 toward the distal-end side. As a result, the pressing force F2 is transmitted along the longitudinal direction of the wire 8, and the wire 8 moves toward the distal-end side.

Once the wire 8 moves toward the distal-end side, the distal-end-side portion 8a of the wire 8 detaches from the outer circumferential surface of the pulley 7 and becomes loose, and the level-difference portion 8c at the border with the proximal-end-side portion 8b abuts against the inclined surface 10 disposed on the proximal-end side of the second gripping piece 6.

In this embodiment, since the proximal-end-side portion 8b of the wire 8 has sufficient flexural rigidity, the proximal-end-side portion 8b does not buckle under the pressing force F2, and the pressing force F2 that has been transmitted through the wire 8 can be applied to the inclined surface 10 of the second gripping piece 6. As shown by the arrows in FIG. 3, the pressing force F2 applied to the inclined surface 10 is broken down in a direction along the tangential line of the inclined surface 10 and in the direction of a perpendicular line to the inclined surface 10. The pressing force component G acting in the perpendicular line direction generates the moment that causes the second gripping piece 6 to be pivoted (clockwise in the drawing) with respect to the first gripping piece 5. As a result, the second gripping piece 6 can be pivoted with respect to the first gripping piece 5 in a direction such that the second gripping piece 6 is opened.

In other words, according to the gripping mechanism 3 and the gripping tool 1 of this embodiment, the two gripping pieces 5 and 6 can be pivoted in both the open direction and the close direction by using a single wire 8. Thus, there is no need to use two wires as in the related art, the diameter of the body portion 2 can be reduced, and a complicated mechanism requiring two wires to open and close the gripping pieces is no longer needed. Thus, there is an advantage in that the structure is simplified and the costs can be reduced.

Figure 4:
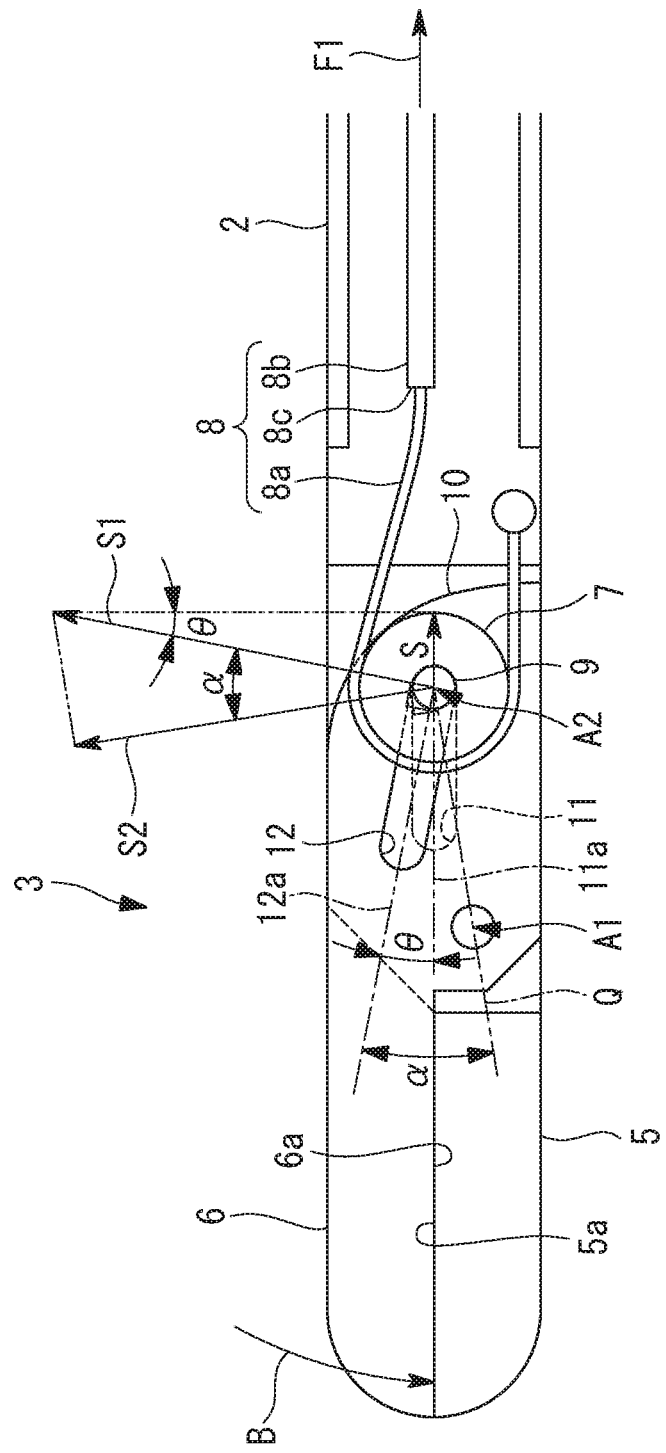
FIG. 4 is a diagram showing a modification of the gripping mechanism shown in FIG. 2, in which the resultant force applied to a pulley when the two gripping pieces are in a closed state and the moment that causes a second gripping piece to be pivoted are shown.
Figure 5:
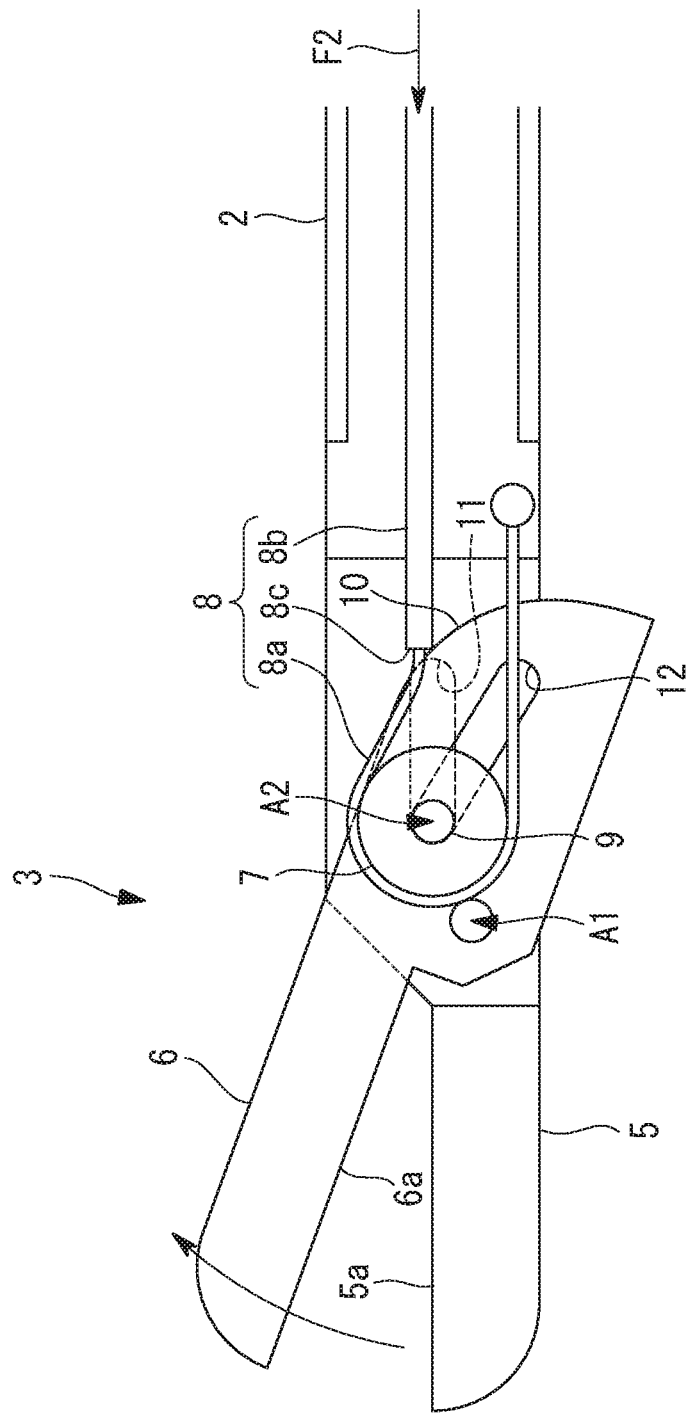
FIG. 5 is a vertical sectional view showing a state in which the two gripping pieces of the gripping mechanism shown in FIG. 4 are open.

It should be noted that, in this embodiment, the pulley 7 is rotatably supported on the shaft 9 secured to the second gripping piece 6; alternatively, as shown in FIGS. 4 and 5, a first elongated hole 11 having a longitudinal axis 11a extending in a front-to-rear direction may be provided in the body portion 2 to which the first gripping piece 5 is secured, a second elongated hole 12 having a longitudinal axis 12a inclined with respect to the longitudinal axis 11a of the first elongated hole 11 may be provided in the second gripping piece 6, and the shaft 9 may be disposed so as to pass through both of the elongated holes 11 and 12 at the position at which the two elongated holes 11 and 12 intersect each other.

As shown in FIG. 4, the first elongated hole 11 provided in the body portion 2 is provided in a straight manner along the longitudinal direction of the body portion 2 at substantially the center of the body portion 2 in the width direction.

Moreover, an angle $\theta$ formed between the longitudinal axis 11a of the first elongated hole 11 and the longitudinal axis 12a of the second elongated hole 12, and an angle $\alpha$ formed between a line segment connecting the pivot axis A1 and the rotation axis A2 and the longitudinal axis 12a of the second elongated hole 12 satisfy the following relational expression:

$$\cos\alpha/\sin\theta > 1 \qquad (1)$$

According to the gripping mechanism 3 having such a configuration, in the resultant force S, a resultant force component S1 orthogonal to the longitudinal axis 12a of the second elongated hole 12 serves as the force that causes the second gripping piece 6 to be pivoted with respect to the first gripping piece 5, and, in the resultant force component S1, the product of an orthogonal component S2 orthogonal to a line segment Q connecting the pivot axis A1 and the rotation axis A2 and the size of the line segment Q serves as the moment that causes the second gripping piece 6 to be pivoted with respect to the first gripping piece 5.

In other words, the resultant force component S1 can be expressed as:

$$S1 \cdot \sin \theta = S \quad (2),$$

and the orthogonal component S2 can be expressed as:

$$S2 = S1 \cdot \cos \alpha \quad (3).$$

Therefore, if $$S2 > S \quad (4),$$

it is possible to generate the orthogonal component S2 in which the resultant force S is amplified, because of the positional relationship between the pivot axis A1 and the angles α and θ of the two elongated holes 11 and 12.

By substituting Expressions (2) and (3) into Expression (4), it is possible to achieve the relationship in Expression (1). As a result, the gripping mechanism 3 according to this embodiment can achieve the resultant force S in which the pulling force F1 is amplified twofold by the action of the pulley 7, and, because Expression (1) is satisfied, there is an advantage in that it is possible to generate a moment in which the resultant force S is additionally amplified.

In the example shown in FIG. 4, as indicated by arrow B, a counterclockwise moment acts on the second gripping piece 6, the second gripping piece 6 is pivoted counterclockwise about the pivot axis A1 with respect to the first gripping piece 5, and thus the gripping surfaces 5a and 6a are closed with respect to each other. Thus, as shown in FIG. 4, tissue can be gripped between the gripping surfaces 5a and 6a of the first gripping piece 5 and the second gripping piece 6.

In this embodiment, the angle α formed between the longitudinal axis 12a of the second elongated hole 12 and the line segment Q connecting the pivot axis A1 and the rotation axis A2 needs to be α<90° regardless of the pivoting angular position at which the second gripping piece 6 is disposed with respect to the first gripping piece 5. In the case in which α=90°, a singular point is formed, and a moment that acts in the direction that causes the two gripping pieces to be closed cannot be generated.

By always achieving α<90°, the closing motion can be carried out with stability.

In addition, with the gripping mechanism 3 according to this embodiment, because the pulley 7 is disposed at substantially the center of the body portion 2 in the width direction and the first elongated hole 11, which defines the sliding pathway of the pulley 7, linearly extends along the longitudinal direction of the body portion 2, there is an advantage in that it is possible to reduce the diameter of the gripping tool 1 by minimizing the influences on the outer diameter of the pulley 7, which limits the outer diameter of the gripping tool 1.

Moreover, in this embodiment, as shown in FIGS. 1 to 5, the pivot axis A1 is disposed by being offset, with respect to the longitudinal axis 11a of the first elongated hole 11, farther in the direction in which the second gripping piece 6 closes with respect to the first gripping piece 5. By doing so, it is possible to ensure a large enough space in the portion closer to the second gripping piece 6 than the pivot axis A1 of the first gripping piece 5, and thus, it is possible to ensure a large enough space for disposing other equipment, such as a sensor, etc.

Alternatively, the pivot axis A1 may be disposed by being offset, with respect to the longitudinal axis 11a of the first elongated hole 11, farther in the direction in which the second gripping piece 6 opens with respect to the first gripping piece 5. By doing so, it is possible to increase the angle at which the second gripping piece 6 is opened with respect to the first gripping piece 5 by an amount corresponding to the degree of offset.

Moreover, it is preferable that the pivot axis A1 be disposed between a distal-end-side extension of the longitudinal axis 11a of the first elongated hole 11 and a distal-end-side extension of the line segment connecting the pivot axis A1 and the rotation axis A2. As a result of the pivot axis A1 being offset farther in the direction of the extension of the longitudinal axis 12a of the second elongated hole 12 with respect to the extension of the longitudinal axis 11a of the first elongated hole 11, it is possible to increase the angle at which the two gripping pieces 5 and 6 are opened with respect to each other, as described above, and, as a result of the pivot axis A1 being brought close to the extension of the longitudinal axis 12a of the second elongated hole 12, it is possible to increase the moment that causes the two gripping pieces 5 and 6 to be closed relative to each other.

In addition, although this embodiment has been described in terms of the case in which the first gripping piece 5 is secured to the body portion 2 and only the second gripping piece 6 is pivoted about the pivot axis A1, alternatively, both the first gripping piece 5 and the second gripping piece 6 may be supported by the body portion 2 so as to be pivotable about the pivot axis A1.

In this case, the second elongated holes 12 that are inclined with respect to the first elongated hole 11 may be provided in both the first gripping piece 5 and the second gripping piece 6, and the longitudinal axes 12a of the two second elongated holes 12 of the gripping pieces 5 and 6 may be inclined in the opposite direction from the longitudinal axis 11a of the first elongated hole 11.

In this case also, by disposing both of the second elongated holes 12 provided in the gripping pieces 5 and 6 so as to satisfy the relationship in the above-described Expression (1), just by applying a small pulling force F1, it is possible to firmly grip, with a large gripping force, the subject, such as tissue, between the two gripping surfaces 5a and 6a by generating the moment by additionally amplifying the resultant force S in which the pulling force F1 applied on the proximal-end side of the wire 8 is amplified approximately twofold by the pulley 7. In addition, by distributing the pivoting angle between the two gripping pieces 5 and 6, it is possible to ensure the angle at which the gripping pieces 5 and 6 are opened is large enough.

In this embodiment, because two portions of the wire 8 wound around the pulley 7 are disposed so as to be substantially parallel to each other, it is possible to cause a force that is twice as great as the pulling force F1 exerted on the wire 8 to act on the pulley 7; however, there is no limitation thereto. In other words, because the resultant force S of the tensile forces T becomes equal to the pulling force F1 when the relative angle of the two portions of the wire 8 is 120°, there is an advantage in that it is possible to amplify the pulling force F1 so long as the two portions of the wire 8 form an angle that is less than 120°. However, in order to achieve an elongated shape of the gripping tool 1, it is preferable that the two portions of the wire 8 be disposed so as to be substantially parallel to each other.

Although this embodiment has been described in terms of the case in which the wire 8 is wound substantially half way around the pulley 7, for example, a return pulley (not shown) having a rotation axis that is parallel to the rotation axis A2 may be provided, and the wire 8 may be wound more than once between the pulley 7 and the return pulley. By doing so, there is an advantage in that it is possible to additionally amplify the pulling force F1.

Figure 6:
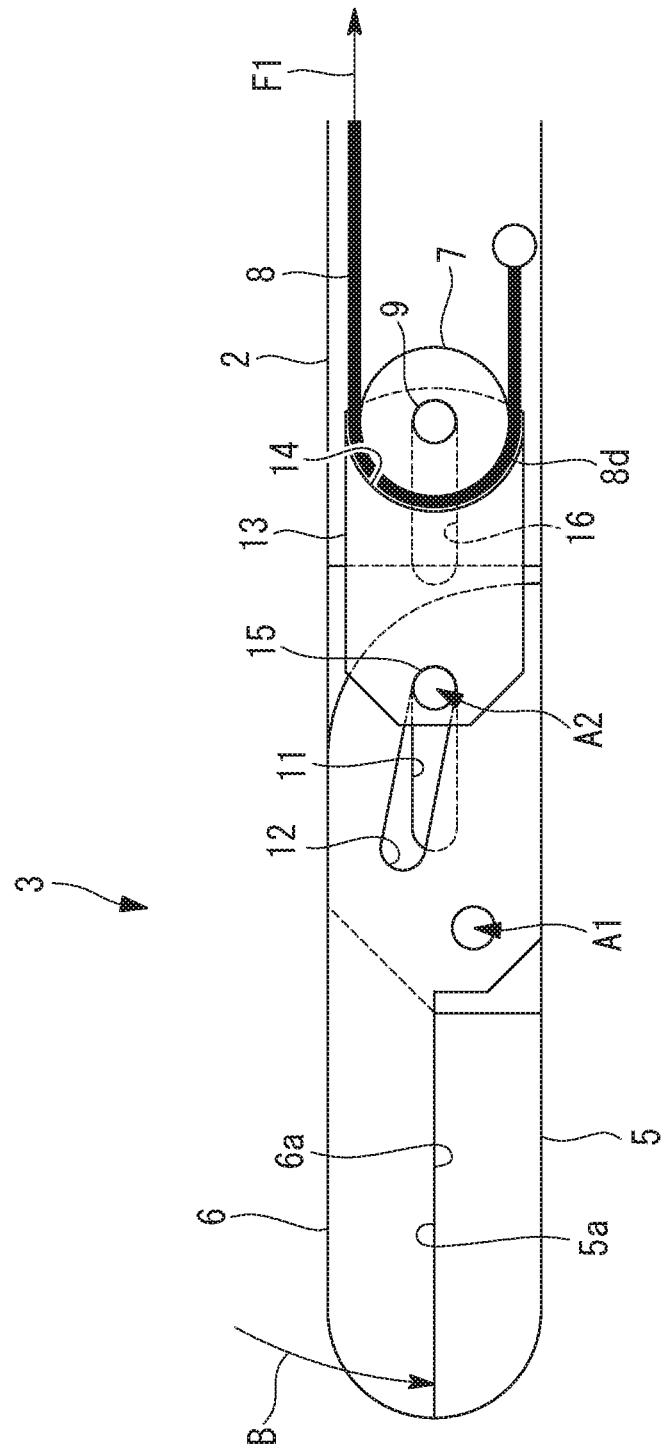
FIG. 6 is a vertical sectional view showing a state in which two gripping pieces of another modification of the gripping mechanism shown in FIG. 2 are closed.
Figure 7:
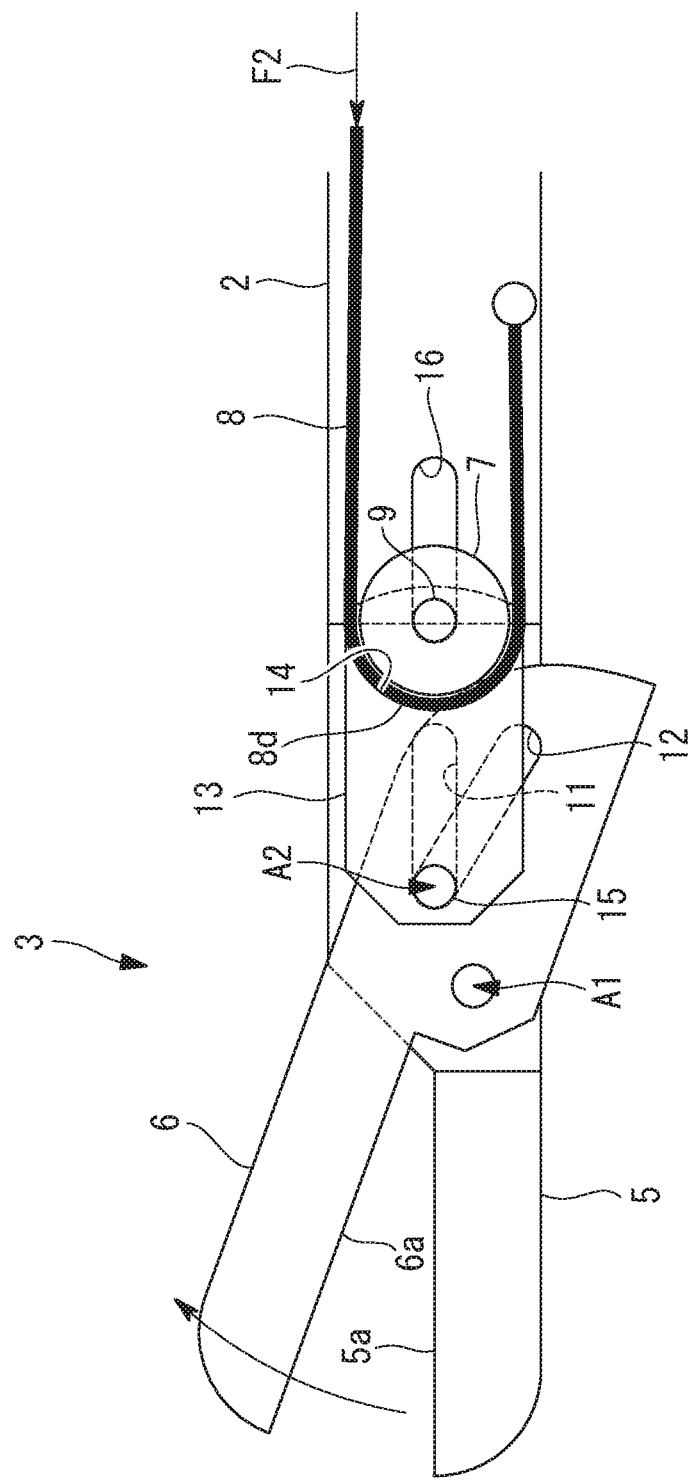
FIG. 7 is a vertical sectional view showing a state in which the two gripping pieces of the gripping mechanism shown in FIG. 6 are open.

In the embodiment described above, the level-difference portion 8*c* between the distal-end-side portion 8*a* and the proximal-end-side portion 8*b* of the wire 8 presses the inclined surface 10 of the second gripping piece 6. Alternatively, as shown in FIGS. 6 and 7, an intermediate member 13, which is movably supported on the body portion 2 along the first elongated hole 11 and to which the shaft 9 that rotatably supports the pulley 7 is secured, may be provided, and a force-receiving portion 14 that receives the pressing force F2 transmitted through the wire 8 may be provided in the intermediate member 13. In the drawings, reference sign 15 denotes a shaft that guides the intermediate member 13 along the elongated holes 11 and 12, and reference sign 16 denotes an elongated hole that guides the shaft 9.

In the example shown in FIGS. 6 and 7, the force-receiving portion 14 is formed of a concave surface located on the distal-end side with respect to the pulley 7. The concave surface is on the radially outer side of the outer circumferential surface of the pulley 7 and faces the outer circumferential surface of the pulley 7.

As shown in FIG. 6, when a pulling force F1 is applied to the wire 8, a wound portion 8*d* wound around the pulley 7 comes into close contact with the outer circumferential surface of the pulley 7 and pulls the shaft 9 toward the proximal end. As a result, the intermediate member 13 moves toward the proximal end, and the two gripping pieces 5 and 6 are closed.

Meanwhile, as shown in FIG. 7, when a pressing force F2 is applied to the wire 8, the wound portion 8*d* wound around the outer circumferential surface of the pulley 7 detaches from the outer circumferential surface of the pulley 7 and comes into close contact with the force-receiving portion 14 disposed radially outward. When the rigidity of the wire 8 is relatively high, despite the absence of the proximal-end-side portion 8*b* having a large outer diameter, the wire 8 transmits the pressing force F2, and the wound portion 8*d* presses the force-receiving portion 14 toward the distal end without buckling under the pressing force F2, and thus the second gripping piece 6 can be pivoted in the direction that causes the second gripping piece 6 to be opened relative to the first gripping piece 5.

Since the force-receiving portion 14 receiving the pressing force F2 is formed of a concave surface, the wound portion 8*d* of the wire 8 is prevented from derailing radially outward, and thus the pressing force F2 can be effectively transmitted.

The force-receiving portion 14 is not limited to a concave surface and may be a flat surface. Moreover, the force-receiving portion 14 is not limited to an arched surface and may have a V-groove shape.

In this embodiment, the wire 8 has a distal-end-side portion 8*a* and a proximal-end-side portion 8*b* that have outer diameters different from each other. Alternatively, these portions may have the same diameter but different flexural rigidity values. The proximal-end-side portion 8*b* of the wire 8 may have a sufficiently higher flexural rigidity than the distal-end-side portion 8*a*, and the proximal-end-side portion 8*b* and the distal-end-side portion 8*a* may have the same diameter.

In this embodiment, the pulley 7 and the force-receiving portion are separate components. Alternatively, the pulley 7 may also serve as the force-receiving portion.

The above-described embodiment leads to the following invention.

One aspect of the present invention provides a gripping mechanism including: two gripping pieces that are pivoted relative to each other about a pivot axis; a base that supports at least one of the gripping pieces at a distal-end portion in a pivotable manner; a pulley that is supported so as to be rotatable about a rotation axis that is parallel to the pivot axis; a wire that is wound around the pulley, in which one end thereof is secured to one of the gripping pieces or the base, and that causes, with a pulling force applied to the other end thereof, tensile forces that move the rotation axis in one direction to act on both sides of the pulley, between which the rotation axis is interposed, the wire transmitting a pressing force applied to the other end; and a force-receiving portion that receives the pressing force transmitted through the wire, wherein the pulley is disposed so that a resultant force of the tensile forces of the wire acting on the rotation axis generates a moment that causes the gripping pieces to be pivoted in a direction that causes the gripping pieces to be closed relative to each other, and the force-receiving portion is disposed so that the pressing force applied from the wire generates a moment that causes the gripping pieces to be pivoted in a direction that causes the gripping pieces to be opened relative to each other.

With this aspect, when the pulling force is applied to the other end of the wire, tensile force that are equal to the pulling force are generated in the wire, and the resultant force of the tensile forces acting in the longitudinal direction of both sides of the wire between which the rotation axis exists is applied to the pulley around which the wire is wound. As a result of this resultant force generating the moment about the pivot axis in a direction in which at least one of the gripping pieces is closed, the two gripping pieces are closed relative to each other, and thus, it is possible to grip a subject, such as tissue, disposed therebetween.

When a pressing force opposite to the pulling force is applied to the other end of the wire, the pressing force is transmitted through the wire and is received by the force-receiving portion. The force-receiving portion generates a moment by the pressing force from the wire and causes the two gripping pieces to be pivoted in a direction that causes the gripping pieces to be opened relative to each other.

In other words, according to this aspect, the two gripping pieces can be closed relative to each other by pulling a single wire, and can be opened relative to each other by a pressing force applied through the same wire; thus, a smaller diameter and reduced costs can be achieved.

In the aspect described above, the pulley may be disposed so that the resultant force of the tensile forces of the wire acting on the rotation axis becomes greater than the pulling force.

In this manner, compared to the case in which a pulling force is directly applied to the position of the rotation axis without the pulley, an amplified force can be applied. In other words, although the pulling force applied to the proximal end of the wire is small, the subject can be gripped with a large force.

In the aspect described above, the base may be provided with a first elongated hole that extends from a distal end toward a proximal end thereof, at least one of the gripping pieces may be provided with a second elongated hole that extends, along a plane that is orthogonal to the pivot axis, in a direction that is inclined in one direction with respect to a longitudinal axis of the first elongated hole, and the rotation axis may be provided so as to be movable in a direction along longitudinal axial directions of the first elongated hole and the second elongated hole.

In this manner, the second elongated hole is pressed in a direction orthogonal to the longitudinal axis thereof by the resultant force component orthogonal to the longitudinal axis of the second elongated hole, the moment is generated about the pivot axis, and the two gripping pieces can be pivoted relative to each other. Since the amplified pulling force is used as the resultant force, the two gripping pieces can be pivoted in the closing direction by means of a large moment despite a small pulling force, and a subject, such as tissue, can be gripped with a large force.

In the aspect described above, the wire may be wound around the pulley at least once.

By doing so, with an increase in the number of times the wire is wound around the pulley, it is possible to increase the resultant force of the tensile forces exerted on the pulley.

In the aspect described above, the wire may include a pressing portion that presses the force-receiving portion, the pressing portion being disposed on a proximal-end side with respect to a portion of the wire wound around the pulley.

In this manner, when the wire is pulled, the resultant force of the tensile forces is generated on both sides of the wound portion wound around the pulley, and due to the resultant force of the tensile forces, a moment can act in a direction in which the two gripping pieces are closed relative to each other. Meanwhile, when the wire is pressed in a direction opposite to the pulling force, the wound portion of the wire becomes loose, the pressing portion on the proximal side with respect to the wound portion presses the force-receiving portion, and a moment can act in a direction in which the two gripping pieces are opened relative to each other.

In the aspect described above, the wire may have a proximal-end-side portion and a distal-end-side portion that interpose the pressing portion, and the proximal-end-side portion has higher rigidity than the distal-end-side portion.

In this manner, because the rigidity in the portion of the wire on the proximal-end side with respect to the pressing portion is high, buckling of the wire is prevented when the pressing portion presses the force-receiving portion, and the pressing force can be more assuredly applied to the force-receiving portion.

In the aspect described above, the proximal-end-side portion of the wire may have an outer diameter greater than an outer diameter of the distal-end-side portion, and a difference in level formed between the proximal-end-side portion and the distal-end-side portion may constitute the pressing portion.

In this manner, since the rigidity can be made different according to the difference in the outer diameter, the same wire wound around the pulley can be easily used to transmit the pressing force to the force-receiving portion.

In the aspect described above, the force-receiving portion may be disposed on an opposite side from the pulley, with a portion of the wire wound around the pulley therebetween.

In this manner, when the wire is pulled, the wound portion is wound around the pulley, and the pulley is pulled. When the wire is pressed in a direction opposite of the pulling force, the wound portion of the wire becomes loose and comes into contact with the force-receiving portion disposed on the opposite side of the pulley. As a result, the wire portion, which has been bent and wound around the pulley, presses the force-receiving portion, and a moment can act in the direction in which the two gripping pieces are opened relative to each other.

In the aspect described above, the force-receiving portion may be formed of a concave surface facing the pulley.

In this manner, the bent portion of the wire can be retained in the force-receiving portion formed of a concave surface so that the bent portion will not spread further, and thus the pressing force can be more assuredly transmitted to the force-receiving portion.

Another aspect of the present invention provides a gripping tool including any gripping mechanism described above, and a driving portion that is connected to the gripping mechanism and that generates the pulling force.

According to this aspect, the operation of opening and closing the two gripping pieces can be performed with a single wire. Since two wires are not needed, the diameter can be reduced, the mechanism can be simplified, and the cost can be reduced.

REFERENCE SIGNS LIST 1 gripping tool
2 body portion (base)
3 gripping mechanism
4 driving portion
5 first gripping piece (gripping piece)
6 second gripping piece (gripping piece)
7 pulley
8 wire
8a distal-end-side portion
8b proximal-end-side portion
8c level-difference portion (pressing portion)
8d wound portion
10 inclined surface (force-receiving portion)
11 first elongated hole
12 second elongated hole
14 force-receiving portion
A1 pivot axis
A2 rotation axis

The invention claimed is:
1. A gripping mechanism comprising:
   a base;
   a first gripping piece secured to a distal end portion of the base;
   a second gripping piece supported by the distal end portion of the base so as to be pivotable about a pivot axis of the first gripping piece;
   a pulley that is supported so as to be rotatable about a rotation axis that is parallel to the pivot axis;
   a wire that is wound around the pulley and in which one end of the wire is secured to the base, the wire causing, with a pulling force applied to an other end of the wire, tensile forces that move the rotation axis in one direction to act on each of opposite sides of the pulley, between which the rotation axis is interposed, and the wire transmitting a pressing force applied to the other end of the wire; and
   a force-receiving surface that receives the pressing force transmitted through the wire,
   wherein the pulley is disposed so that a resultant force of the tensile forces of the wire acting on the rotation axis generates a moment that causes the second gripping piece to be pivoted in a direction that causes the second gripping piece to be closed relative to the first gripping piece, and the force-receiving surface is disposed so that the pressing force applied from the wire generates a moment that causes the second gripping piece to be pivoted in a direction that causes the second gripping piece to be opened relative to the first gripping piece.

2. The gripping mechanism according to claim 1, wherein the pulley is disposed so that the resultant force of the tensile forces of the wire acting on the rotation axis becomes greater than the pulling force.

3. The gripping mechanism according to claim 1,
wherein the base is provided with a first elongated hole that extends from a distal end toward a proximal end thereof,
at least one of the first gripping piece and the second gripping piece is provided with a second elongated hole that extends, along a plane that is orthogonal to the pivot axis, in a direction that is inclined in one direction with respect to a longitudinal axis of the first elongated hole, and
the rotation axis is provided so as to be movable in a direction along longitudinal axial directions of the first elongated hole and the second elongated hole.

4. The gripping mechanism according to claim 1, wherein the wire is wound around the pulley at least once.

5. The gripping mechanism according to claim 1, wherein the wire includes a pressing surface that presses the force-receiving surface, the pressing surface being disposed proximally with respect to a portion of the wire wound around the pulley.

6. The gripping mechanism according to claim 5, wherein the wire has a proximal-end-side portion and a distal-end-side portion that interpose the pressing surface, and the proximal-end-side portion has higher rigidity than the distal-end-side portion.

7. The gripping mechanism according to claim 6, wherein the proximal-end-side portion of the wire has an outer diameter greater than an outer diameter of the distal-end-side portion, and
a difference between the outer diameter of the proximal-end-side portion and the outer diameter of the distal-end-side portion comprises the pressing surface.

8. The gripping mechanism according to claim 1, wherein the force-receiving surface is arranged to oppose the pulley, with a portion of the wire wound around the pulley therebetween.

9. The gripping mechanism according to claim 8, wherein the force-receiving surface is a concave surface facing the pulley.

10. A gripping tool comprising:
the gripping mechanism according to claim 1; and
an actuator operatively connected to the wire, the actuator being configured to generate the pulling force.

* * * * *